United States Patent
Raatz, Jr. et al.

[11] 3,977,236
[45] Aug. 31, 1976

[54] APPARATUS AND METHOD FOR ULTRASONIC FASTENER HOLE INSPECTION

[75] Inventors: Charles F. Raatz, Jr.; Russell K. Woodbury; Wayne E. Woodmansee, all of Seattle, Wash.

[73] Assignee: The Boeing Company, Seattle, Wash.

[22] Filed: Oct. 21, 1974

[21] Appl. No.: 516,538

[52] U.S. Cl. .............................................. 73/67.8 S
[51] Int. Cl.² ........................................... G01N 29/04
[58] Field of Search ......... 73/67.8 S, 67.9, 71.5 US, 73/67.8 R, 67.7, 67.5 R

[56] References Cited
UNITED STATES PATENTS

| | | |
|---|---|---|
| 2,666,862 | 1/1954 | Branson ........................ 73/71.5 UX |
| 2,893,239 | 7/1959 | Renaut ................................. 73/67.7 |
| 3,533,278 | 10/1970 | Valkenburg ..................... 73/67.8 R |
| 3,721,118 | 3/1973 | Jeffras .............................. 73/67.8 S |
| 3,809,607 | 5/1974 | Murray et al. ................ 73/67.8 S X |
| 3,863,496 | 2/1975 | Hiramatsu ....................... 73/67.8 S |

*Primary Examiner*—James J. Gill
*Attorney, Agent, or Firm*—Morris A. Case; Bernard A. Donahue

[57] ABSTRACT

An ultrasonic scanner positions a transducer with respect to a fastener hole, with an installed fastener, to adjustably control transducer direction and location and to maintain transducer contact while scanning the hole. The scanner synchronizes transducer location during scanning cycle and transmits ultrasonic echoes from the transducer into a storage display monitor to detect flaws.

13 Claims, 14 Drawing Figures

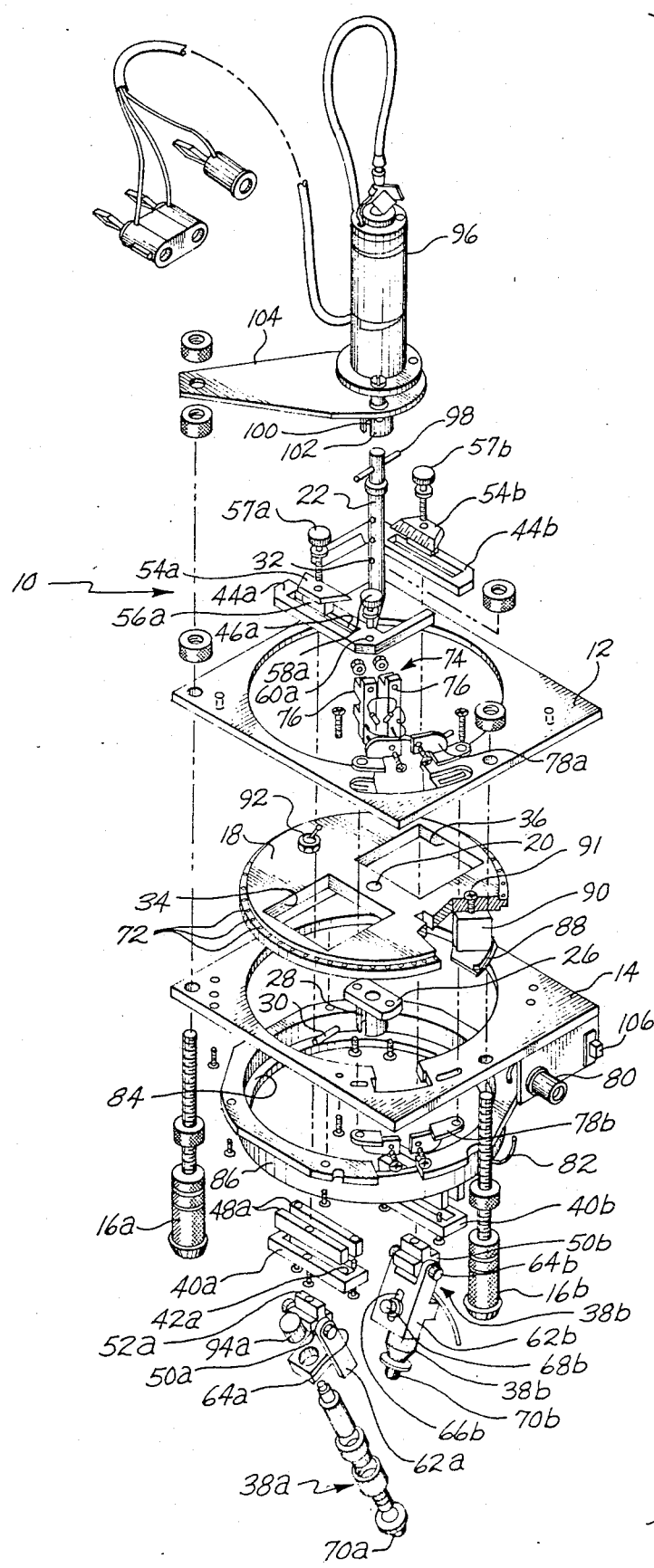

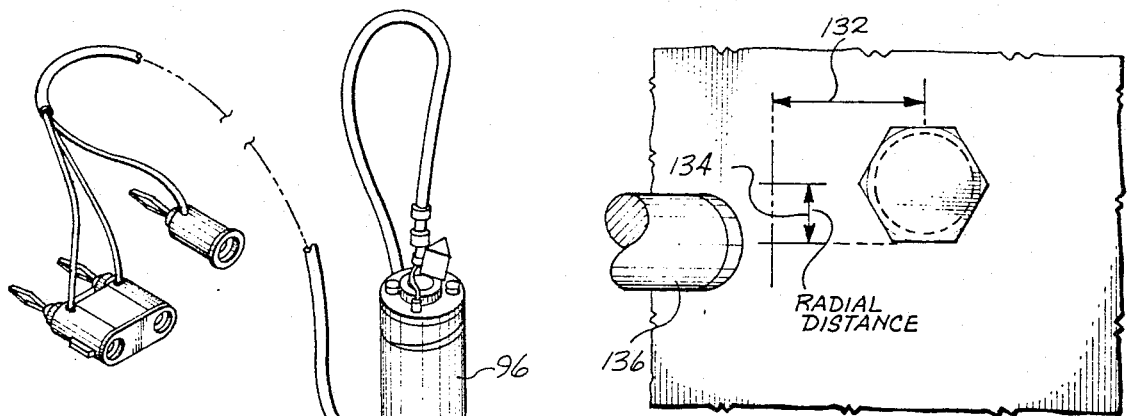
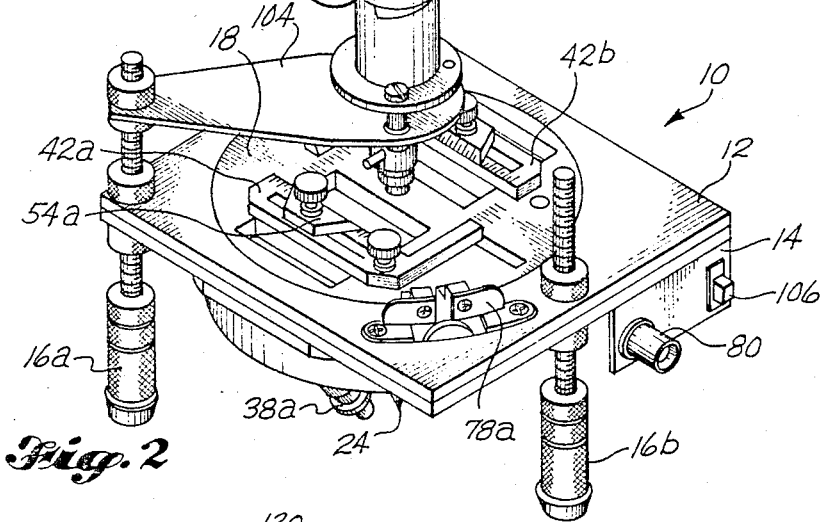
Fig. 5
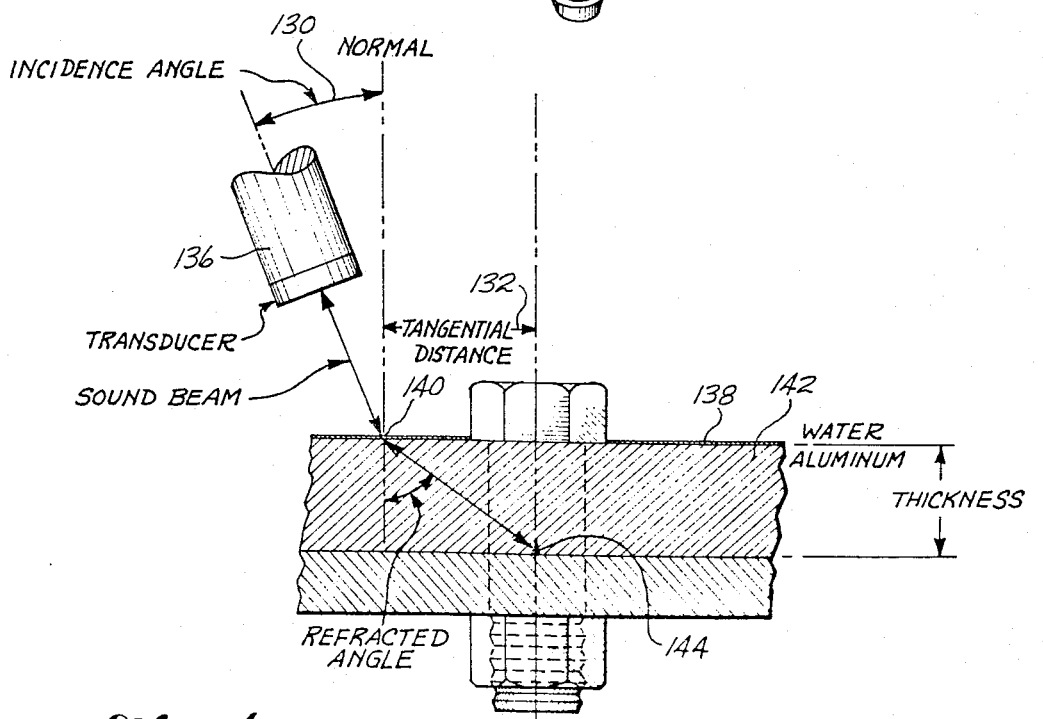
Fig. 2
Fig. 4

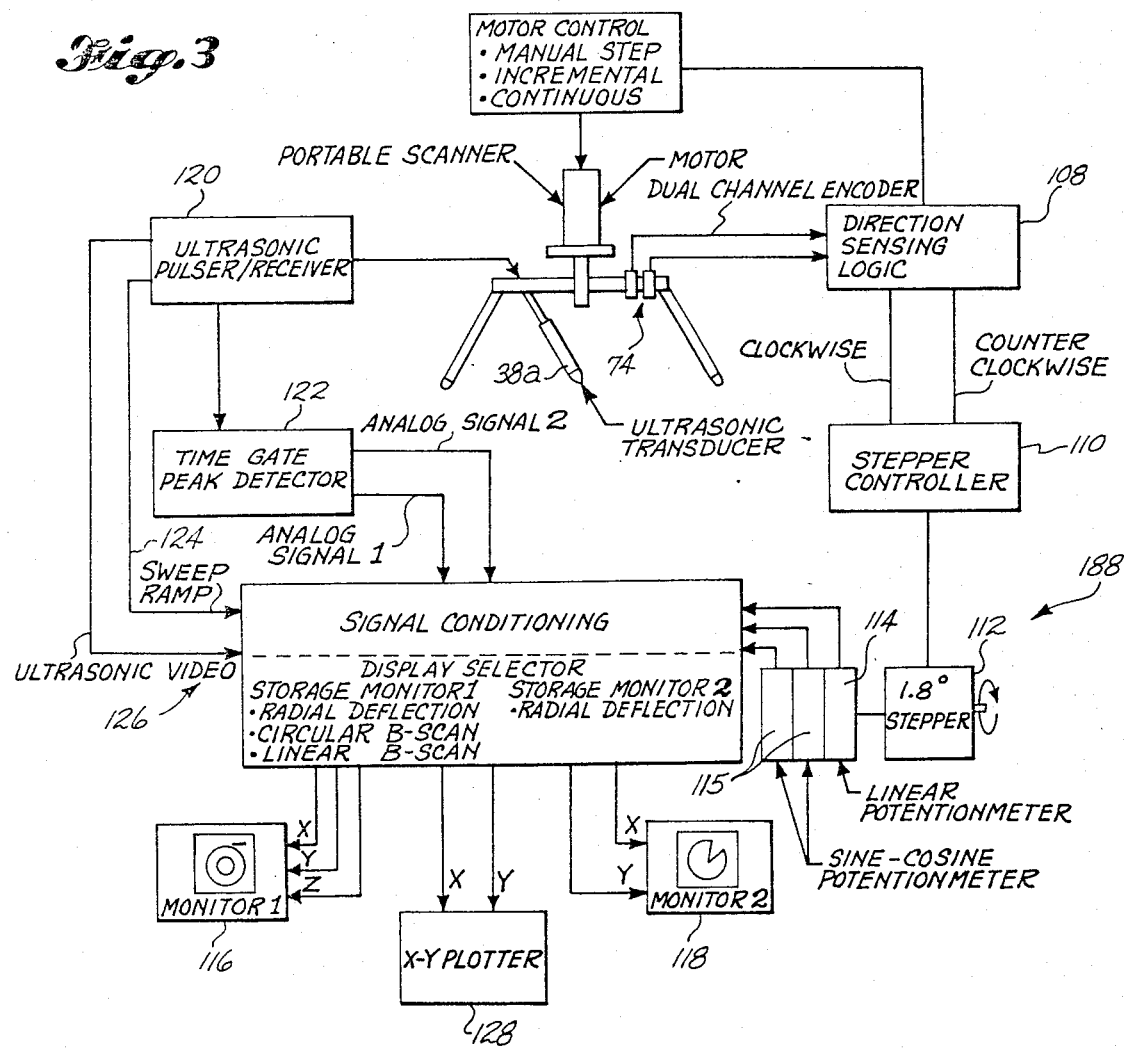
Fig. 3
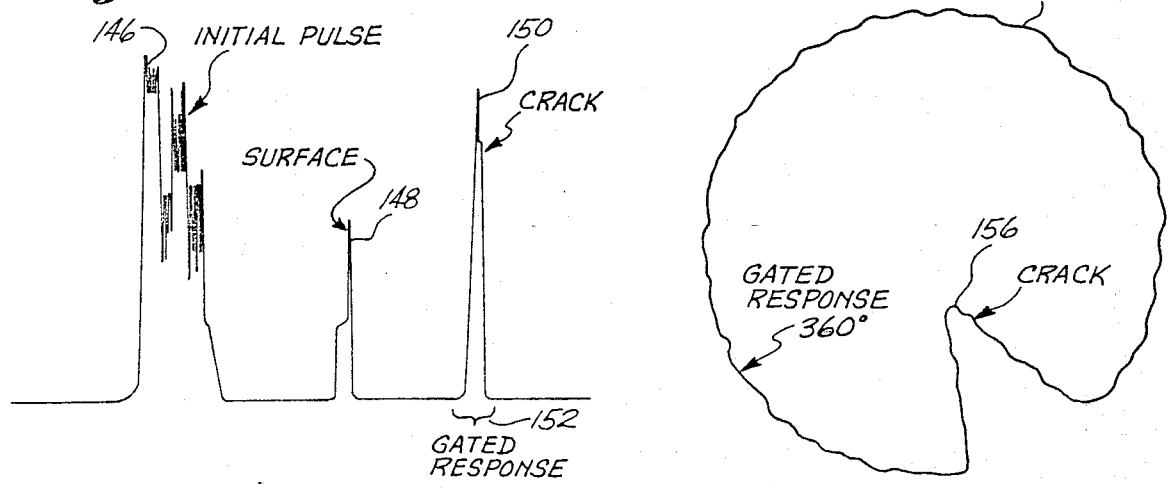
Fig. 6
Fig. 7

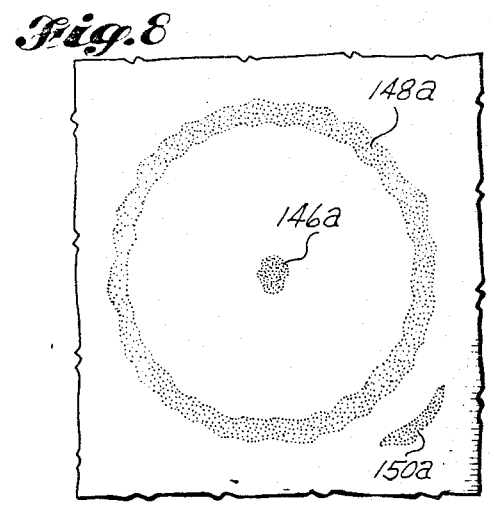
Fig. 8
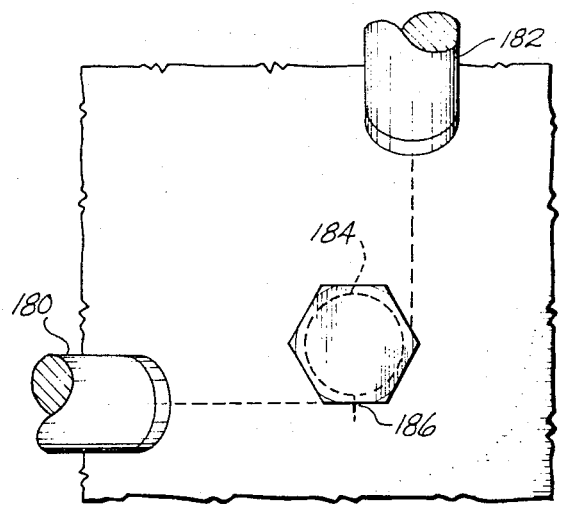
Fig. 10
Fig. 9
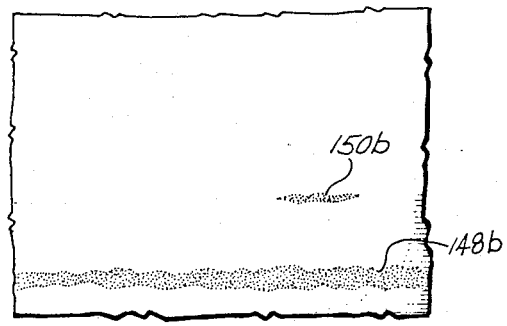
Fig. 13
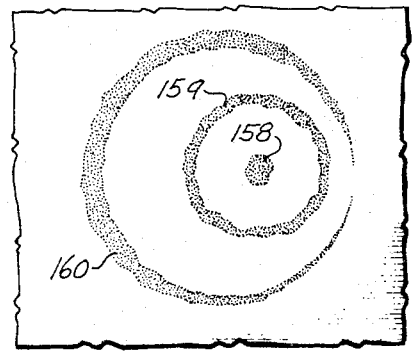
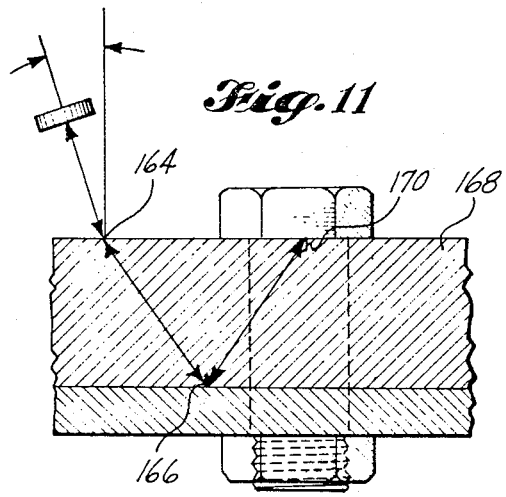
Fig. 11
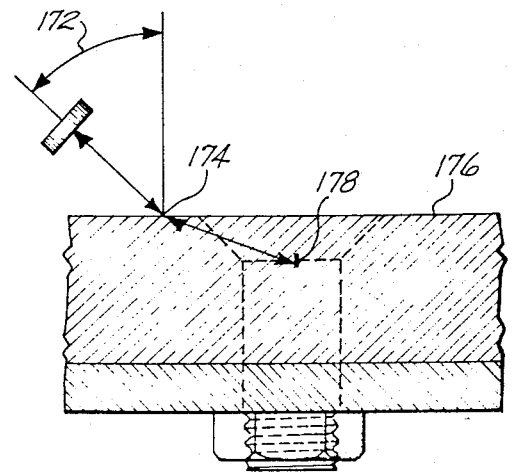
Fig. 12
Fig. 14
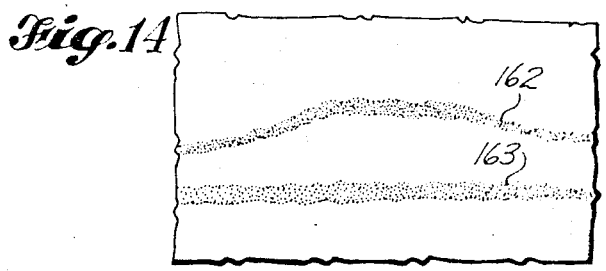

APPARATUS AND METHOD FOR ULTRASONIC FASTENER HOLE INSPECTION

The invention described herein may be manufactured and used by or for the Government of the United States of America for governmental purposes without the payment of any royalties thereon or therefore.

BACKGROUND OF THE INVENTION

Structures of all types are susceptible to fatigue cracks that generally initiate at fastener holes. The causes of initiation are many and varied. Early detection of fatigue cracks and corrective action combine to mitigate the risks and the expense of maintaining structures. Present inspection methods for fatigue cracks generally depend on either the crack being sufficiently large for its detection by visual or radiographic methods, or they require the removal of the fastener to locate smaller cracks or flaws using eddy currents. The cost of hole inspection includes not only the time of removal and replacement, but also a factor for possible damage incurred solely from the act of removal.

It is known to use ultrasonic means to inspect for flaws in bodies. In U.S. Pat. No. 3,280,621 there is a search mechanism for detecting flaws in metal where several transducers are arranged in a holding head capable of being spun. The spinning head holding the transducers moves over the material to be checked while both head and material to be tested are immersed in a fluid. U.S. Pat. No. 3,431,774 also tests, in this case, sheet material immersed in a liquid medium with a moving rotating head adapted to generate a plurality of ultrasonic beams while immersed in the liquid. These patents are typical of ultrasonic testing devices in that a transducer and material to be tested are both immersed in a fluid and the transducer rotates while moving over the material to be tested, and thus inspects a large area of material.

SUMMARY OF THE INVENTION

A scanning device has an adjustable mounting with a rotatable carriage. The carriage is driven with a shaft that may be positioned to center on the axis of a hole containing an installed fastener. A transducer mounted to the carriage has an adjustable mounting to permit control of the transducer direction, positioning with respect to tangential and radial distances from the hole axis, and to permit intimate contact with the working surface of the part to be tested. A liquid film is placed between a boot on the transducer and the working surface to assure sonic contact. A series of equally spaced holes adjacent the edge or rim of the carriage or carrier work in conjunction with an electro-optical encoder positioned on the mounting or frame to generate electrical impulses synchronized to the transducer location. A control and display unit energizes the transducer and receives back echo signals. Echoes from a flaw are time gated to deflect the radial image on a storage monitor, said radial image being imparted by the electrical impulses from the encoder. A second monitor simultaneously driven by electrical impulse from the encoder may selectively impart a radial A-scan or a B-scan on the monitor from echoes transmitted from the transducer.

DESCRIPTION OF THE DRAWINGS

FIG. 1 shows an exploded view of the scanner.

FIG. 2 shows a perspective view of FIG. 1.

FIG. 3 is a schematic of the scanner with control and displays.

FIG. 4 shows a fragmented side elevational view of positioning of a transducer for ultrasonic inspection of a crack in a fastener hole with an installed fastener.

FIG. 5 is a plan view of the transducer and fastener of FIG. 4.

FIGS. 6, 7, 8 and 9 show various recordings of the crack of FIG. 4 with FIG. 6 being an A-scan recording, FIG. 7 a time gated radial deflection, FIG. 8 a radial B-scan and FIG. 9 a linear B-scan.

FIG. 10 shows a variation of the ultrasonic inspection of FIG. 5 with a pair of mounted transducers to ultrasonically approach a potential crack from opposite sides.

FIG. 11 shows a fragmented elevational view as in FIG. 4 with the transducer directed to detect a flaw or crack around the top surface of a fastener hole.

FIG. 12 shows a fragmented elevational view as in FIG. 4 with the transducer directed to detect a flaw or crack around the base of a countersink hole.

FIG. 13 shows a circular B-scan of the fastener hole when the scanner is not centered on the fastener hole.

FIG. 14 shows a linear B-scan of the fastener hole when the scanner is not centered on the fastener hole.

DETAILED DESCRIPTION

Scanner 10 has a pair of bearing plates 12 and 14 which make up a mounting frame. These bearing plates are adjustably mounted by three adjustable legs two of which are seen at 16a and 16b. The bearing plates provide the holding and working surface for a rotatable carrier or carriage 18 which preferably is disk shaped. The carriage has axial hole 20 sized to accept a centering drive shaft 22. The drive shaft is sharply pointed at 24 to allow visual centering of the scanner. Boss 26 fastens to the carriage. The boss is slotted at 28 and pin 30 extends through hole 32 of the shaft to tie the carriage to the drive shaft. In this embodiment the carriage has rectangular shaped holes 34 and 36 for adjustably holding transducers 38a and 38b. Sliding crossway 40a extends across the bottom of carriage hole 34 and has longitudinal slot 42a. L-shaped calibrated sliding crossway 44a extends across the top of carriage hole 34 and has longitudinal slot 46a. Raceways 48a fasten to crossway 40a located below the carriage and to crossway 44a located above the carriage. The raceways are spaced apart the same distance as the width of the slot 42a and the slot 46a, and are of a length to fit up inside opening 34 in the carrier to provide a sliding fit along the walls of the opening. Lower slide 50a has projection 52a to slideably fit in slot 42a and of a width to permit lateral movement within the slot. Upper slide 54a has projection 56a to slideably fit in slot 46a and also of a width to permit lateral movement within the slot. Bolt 57a extends through the upper slide and threads into the lower slide. When this bolt is loosened the slides may be moved laterally within the slots and locked in position when the bolt is tightened. Bolt 58a threads into opening 60a and against the carriage to lock the crossways in position. When this bolt is loosened the sliding crossways with the slide may be moved toward or away from the axis of the carriage. Transducer carrier 62a is pivotally connected to lower slide 50a with bolt 64a to permit adjusting the angle at which the transducer is directed toward a working surface. In this embodiment the transducer device 38b is adjustably mounted with similar supporting members shown for supporting transducer device 38a with comparable numbers followed by the letter b. In both transducer devices the height of transducer is controlled by adjustment to legs 16a, 16b and 16c and in addition slot 66b in transducer carrier 62b permits another adjustment of transducer height by moving bolt 68b within the slot and tightening against the side of the transducer. A rubber boot 70a fits on the bottom of transducer device 38a and rubber boot 70b fits on the bottom of transducer device 38b. The boot preferably has a rounded bottom, uses about a 60 durometer neoprene and has bottom thickness of about 0.006 inches. The carriage 18 has a plurality of equally spaced holes 72 located adjacent the rim of the carriage. In this embodiment 200 holes were used. An electro-optical encoder 74 consists of two photoelectric sensors 76 mounted to the bearing plates with brackets 78a and 78b. The sensors' light beams are alternately detected by passing through one of the 200 holes in the rim of the carriage to generate electrical pulses. Electrical signals to and from the transducers pass through connector 80, wire 82 and onto slip ring 84 located on support 86. From the slip ring the electrical signals are picked up by multifiber brass brush 88 whose mount 90 is attached to the carriage 18 with a single screw 91 to permit adjustment of brush pressure. Signals from the brush are connected by a wire not shown to transducer selector switch 92, and thence to transducer connection caps 94a and 94b. The selector switch in this embodiment allows selection of either transducer and also has a common ground lug for the transducers. The ground path for signals is from the barrel of the connector to the bearing plates 12 and 14 which have a sliding contact with the carrier disk.

The centering drive shaft may be rotated by hand or may be driven by motor 96. Transverse pin 98 fits in slot 100 of cylinder 102 which is driven by the motor. The motor is supported by mounting plate 104 which attaches to leg 16a. When the motor drive is used, the scanner may be turned continuously in either direction or be programmed to rotate a selectable angular increment and then automatically stop. Unit 106 is a connector for motor control and data display.

FIG. 3 shows a schematic of the scanner, controls and display for the scanner. As the carriage on the scanner rotates electrical pulse signals from the photo sensors go through direction sensing logic unit 108, stepper controller 110 and stepper motor 112. The stepper motor drives potentiometers which include linear potentiometer 114 and also sine-cosine potentiometers 115 to impart an image on storage display monitors 116 and 118. When the linear potentiometer is being used the display on the monitors' oscilloscope will be lineal, and when the sine-consine potentiometers are used the image will be radial. Thus the image will reflect position of the carriage holding the transducers.

Ultrasonic pulser/receiver 120 transmits electrical signals to the transducer and receives back echo signals from the transducer. For monitoring echoes from a flaw or crack in a fastener hole the signal passes through a time gate 122 thence into storage display monitor to deflect the image on the storage display monitor when a flaw is detected. Echo signals received back through the pulser/receiver also generate signals for sweep ramp 124 and for ultrasonic video 126. The sweep ramp is used to generate B-scans to sweep in synchronism with the ultrasonic instrument A-scan display. The video is used to intensity modulate the Z-axis of the storage monitors in forming the B-scans in response to detected echo signal peaks. An X – Y plotter 128 may be used to chart the image generated through the time gate, however, it is preferable to reproduce the image by taking a picture of the stored image as it is faster. One may transmit through one transducer and receive an echo back through a second transducer, however, it is preferred to use a single transducer to both transmit and to receive.

For inspecting fastener holes, defects, if any, are usually located in a straight bore hole, either at the top or the bottom surface of the material. If the hole is countersunk the crack may also be at the base of the countersink. Thus, the transducer is directed and located to obtain the desired path for the sound travel. In FIG. 4 the transducer is directed for inspection of a flaw at the lower surface of the material, FIG. 11 for inspection of a flaw at the upper surface of the material, and FIG. 12 for inspection of a flaw at the base of a countersink hole. It would be possible to direct the transducer in FIG. 12 to bounce the sound off the lower surface, but it was found preferable to go directly to the flaw. The angle of incidence 130 shown in FIG. 4 may vary considerably. When the tangential distance 132 is kept short, as is desirable when fastener holes are close together, this angle for inspecting for either top or bottom flaws may vary from about 8° to 26.5° with about 15° to 24° preferred. The radial distance 134 as best shown in FIG. 5 varies according to the size of hole. In FIG. 4 the transducer 136, transmits and receives ultrasonic waves through water in the inside of the transducer holder and the boot, neither of which is shown in this view. The boot contacts working surface 138 at point 140. The sound is refracted within material 142 toward crack 144, and echoes travel back along the same lines to the transducer. An A-scan of the flaw in FIG. 4 is illustrated in FIG. 6. Peak 146 shows the initial pulse at the transducer, peak 148 shows the echo from the surface of contact at 140 and peak 150 reflects an echo from crack 144. To inspect the fastener hole a time gate illustrated as 152 limits the deflection peaks to the time period for the echoes returning from the area of suspected crack. FIG. 7 illustrates the example using a radial trace 154 wherein only one crack was detected around the periphery of the hole as indicated by inward deflection 156. The monitor may alternately be set to deflect outward in response to the crack echo signal. In FIG. 8 it shows a radial B-scan of the deflections shown in A-scan FIG. 6. The sweep ramp 124 brings in all the signals with the center trace 146a showing zero time to reflect the initial pulse, surface echo 148a and crack echo 150a. FIG. 9 shows a linear B-scan of the deflections shown in A-scan FIG. 6. The zero time or initial pulse deflection is set so that it does not record, but the surface echo 148b and the crack echo 150b are as shown. The ultrasonic video effect on both FIGS. 8 and 9 is to give brightness to strong echoes. Thus, if the transducer boot is not making good contact with the working surface at 140, the echo trace at 148a and 148b would be considerably brightened to show poor contact with the working surface.

With a flush head bolt which is hidden by paint or other covering the B-scan such as the radial scan of FIG. 13 or the lineal scan of FIG. 14 is used to be certain the scanner is properly centered on the axis of the hole. In FIG. 13 the scanner is found off-center as shown by the relation of the initial pulse trace 158 and the surface pulse trace 159 with respect to the hole trace 160 and the lack of signal on part of the hole trace. It is preferable when checking hole location to direct the transducer toward the hole with zero radial distance. In FIG. 14 the lineal trace 162 of the hole periphery is curved instead of a horizontal line as is surface trace 163 which indicates the scanner is not centered on the axis of the hole.

In FIG. 11 the sound waves echo back from the transducer contact point 164 with the working surface, the lower surface 166 of the material 168 and flaw 170 located under the top surface of the material around the fastener hole.

As shown in FIG. 12 it was found best to increase the transducer angle of incidence 172 to about 26° and locate the point of transducer contact 174 with the working surface 176 close to the fastener hole to send the sound directly to the flaw 178 at the base of the countersink.

It was found that certain types of cracks display better echoes when the ultrasonic wave approaches from one side of the crack instead of the other. FIG. 10 shows two transducers 180 and 182 that may be simultaneously mounted in a carriage to direct sound waves to inspect a fastener hole 184 wherein one transducer directs sound waves to approach crack 186 from the side opposite the side approached by sound waves from the first transducer.

In operation a transducer 38a is set at an angle to obtain the angle of incidence desired and the transducer carrier 62a locked in position by tightening bolt 64a. Next, bolts 57a and 58a are loosened and the slides and sliding crossways moved to obtain tangential and radial positioning of the boot of the transducer with respect to the axis of the centering shaft 22. Next, the height of the frame and of the transducer is adjusted to insure transducer boot contact with the working surface. A liquid material such as glycerine and water or an oil is placed either upon the boot or the working surface to insure sonic contact. Next, the scanner is positioned with the point 24 of the shaft 22 centered on the axis of the fastener hole. The control and display unit 188 is energized to operate the scanner and record the results of the scan.

Once the scan of a fastener hole is complete the scanner is moved to center on the axis of the next hole, and energized to inspect that hole. The stored trace may be automatically removed once the unit is energized to scan the second hole and thus not interfere with the stored trace of the second hole.

A second transducer 38b may be mounted in the rectangular shaped opening 36 of carrier 18 as shown in this embodiment.

We claim:

1. An apparatus to inspect a fastener hole without removing the fastener comprising: a scanner including, an adjustable mounting, means for adjustably fastening a transducer to the mounting with said transducer capable of transmitting and receiving ultrasonic energy, means for directing the transducer around a fastener hole, means for rotating the transducer around the fastener hole, and means for sensing transducer location and direction; and means for storage display of echo signals received by the transducer.

2. An apparatus to inspect fastener holes without removing the fastener as in claim 1 further comprising means for monitoring the scanner to assure contacting a working surface around a fastener hole with the transducer and for centering on the hole.

3. An apparatus as in claim 2 wherein the means for adjustably fastening the transducer includes: means for adjusting the transducer height and angle of incidence, and means for adjusting tangential distance and for adjusting radial distance of the transducer with respect to the hole centerline.

4. An apparatus as in claim 3 wherein the means for sensing transducer location and direction includes: a rotatable carrier disk to which the transducer is mounted, said disk having equally spaced holes adjacent the outer rim; and means for electro-optical encoding in combination with the holes in the disk to generate electrical impulses.

5. An apparatus as in claim 4 further including a second ultrasonic transmitting and receiving transducer adjustably mounted to the disk in a position to direct sound waves to approach fastener hole defects from a side opposite the side approached by sound waves from the first transducer.

6. An apparatus for ultrasonic inspection of a fastener hole without removing the fastener, the apparatus having a scanning device comprising: an adjustable frame, a circular carrier rotatably mounted in the frame, means for adjustably mounting and directing in the carrier at least one transducer capable of ultrasonic transmitting and receiving, means for rotating the carrier, and means for converting carrier rotation into electrical pulses; and the apparatus also having a control and display device comprising: means for utilizing the electrical pulses to control a stepper motor to drive potentiometers and impart a radial image on a storage display monitor, means for transmitting a pulse to and for receiving ultrasonic echoes from the transducer, means for utilizing the signal from the echo through a time gate for imparting deflection to the radial image in response to flaws detected.

7. An apparatus as in claim 6 further comprising: a second storage display monitor; means for imparting a radial image on the second monitor from the driven potentiometers; means for imparting sweep ramp B-scans, in response to transducer echoes, to the radial image, and means for utilizing detected echo signal peaks for intensity modulating the B-scans.

8. An apparatus as in claim 6 further comprising: a second storage display monitor, means for imparting a linear image on the second monitor from the driven potentiometers, means for imparting sweep ramp B-scans in response to transducer echoes to the lineal image, and means for utilizing detected echo signal peaks for intensity modulating the B-scans.

9. An apparatus as in claim 6 further comprising: a second transducer adjustably mounted to the carrier positioned to direct sound waves to approach fastener hole defects from a side opposite the side approached by sound waves from the first transducer.

10. An apparatus for ultrasonic inspection of a fastener hole without removing the fastener comprising: an adjustable frame; a circular carriage rotatably mounted to the frame; means for adjustably mounting a transducer, capable of ultrasonic transmitting and receiving, to the carriage, said means including means for adjusting transducer height and angle of incidence, and tangential and radial position of the transducer with respect to fastener hole axis; a plurality of equally spaced holes located on the carriage; means for rotating the carriage; means for electro-optical encoding in combination with the holes to generate electrical pulses; means for utilizing the electrical pulses to detect transducer location and impart an image on a storage display monitor; means for transmitting a pulse to and for receiving ultrasonic echoes from the transducer; means for utilizing the signal from the echo through a time gate to impart deflection to the image in response to flaws detected.

11. An apparatus for ultrasonic inspection of a fastener hole as in claim 10 further comprising: a second transducer adjustably mounted to the carriage to direct sound waves to approach fastener hole defects from a side opposite the side approached by sound waves from the first transducer.

12. A method of ultrasonic inspection of a fastener hole with the fastener in position using a scanner and a control and display unit the steps comprising: directing and locating a transducer, adjustably mounted to a rotatable carriage part of a scanner, with respect to axis of rotation of the carriage; positioning the scanner with the carriage axis of rotation located over axis of a fastener hole to be inspected, rotating the carriage; utilizing an electro-optical encoder for sensing carriage position and introducing electrical impulses into a storage monitor; introducing an ultrasonic pulse into the transducer and receiving an echo signal back from the transducer; and utilizing a time gate for transmitting the echo signal from a hole flaw for deflecting the signal in the storage monitor in response to the echo from the flaw.

13. A method of ultrasonic inspection of a fastener hole as in claim 12, further steps comprising: utilizing a second transducer directed and positioned for directing an ultrasonic signal to approach the flaw in the fastener hole from a side opposite the side the signal approaches from the first transducer.

\* \* \* \* \*